United States Patent
Mellul et al.

[11] Patent Number: 5,985,297
[45] Date of Patent: *Nov. 16, 1999

[54] ANHYDROUS AND WATER-RESISTANT COSMETIC COMPOSITIONS

[75] Inventors: Myriam Mellul, L'Hay-Les-Roses, France; Paul Thau, Berkely Heights, N.J.; Paul Fehn, Westfield, N.J.; Carlos Pinzon, Hackensack, N.J.

[73] Assignee: L'Oreal, France

[*] Notice: This patent is subject to a terminal disclaimer.

[21] Appl. No.: 09/138,379

[22] Filed: Aug. 24, 1998

Related U.S. Application Data

[63] Continuation of application No. 08/882,298, Jun. 25, 1997, Pat. No. 5,184,316, which is a continuation of application No. 08/538,046, Oct. 2, 1995, abandoned.

[30] Foreign Application Priority Data

Sep. 30, 1994 [FR] France ................................ 94-11743

[51] Int. Cl.[6] ................................................ A61K 7/48
[52] U.S. Cl. .......................... 424/401; 424/59; 424/62; 424/70.1; 424/78.03; 514/844; 514/944
[58] Field of Search ................................ 424/401, 59, 62, 424/70.1, 78.03; 514/844, 944

[56] References Cited

U.S. PATENT DOCUMENTS 5,496,544  3/1996  Mellul et al. ..................... 424/78.03
5,849,316  12/1998  Mellul et al. ..................... 424/401

FOREIGN PATENT DOCUMENTS 0133963  3/1985  European Pat. Off. .
0521647  1/1993  European Pat. Off. .
0548694  6/1993  European Pat. Off. .
2688134  9/1993  France .

OTHER PUBLICATIONS

Derwent Abstract of FR–A–2688134.

*Primary Examiner*—Jyothsna Venkat
*Attorney, Agent, or Firm*—Finnegan, Henderson, Farabow, Garrett & Dunner

[57] ABSTRACT

An anhydrous, water-resistant cosmetic composition comprising silicone-containing materials, fillers and pigments. This composition may be used as a make-up product or as a hair product.

17 Claims, No Drawings

ANHYDROUS AND WATER-RESISTANT COSMETIC COMPOSITIONS

This is a continuation of application Ser. No. 08/882,298, filed Jun. 25, 1997 now U.S. Pat. No. 5,849,316, which is a continuation of application Ser. No. 08/538,046, filed Oct. 2, 1995, now abandoned.

The invention is directed to anhydrous and water-resistant make-up compositions comprising, inter alia, at least one silicone gum.

Water-resistant compositions in water-in-oil or water-in-silicone emulsion form are known in the prior art. The use of such emulsions relies on the fact that after spreading, the water evaporates and the oil or the silicone remains in contact with the skin, giving a water-resistant make-up. However, the application of such compositions has the drawback of leaving the skin with an oily appearance and of giving a greasy feel. The result obtained after application is not really natural, and the make-up shines or becomes shiny.

Another form of water-resistant cosmetic compositions is a composition in which fillers, including pigments, are introduced into a volatile or non-volatile silicone oil. The major drawback of this type of composition lies in the stretching effect on the skin, and in the unpleasant, dry sensation which appears after application. Furthermore, the effect sought in the use of such compositions containing pigments, namely a coloration of the skin, is often not achieved. The very nature of the composition is such that the distribution of the pigments in the composition after spreading is not homogeneous; the pigments spread more or less uniformly and tend to agglomerate in the pores and the folds in the skin. This effect runs counter to the search for a coloration close to that obtained naturally.

In all cases, the compositions obtained have faults both with regard to the stability and with regard to the homogeneity of the dispersion of the pigments. Solutions to these problems have been proposed, such as, for example, the use of water-soluble dyes or of dihydroxyacetone (DHA). In the case of water-soluble dyes, the make-ups obtained are not water-resistant and are not perfectly homogeneous.

Products using DHA are difficult to formulate, on account of the degradation and the incompatibility of DHA with many components usually used in compositions of this type. In addition, a major drawback of DHA, in its use in cosmetic compositions, lies in the development of unpleasant odors during ageing.

An object of the present invention is to provide solutions to the various problems encountered in the applications of the prior art and to propose a cosmetic composition possessing good water resistance and at the same time possessing good cosmetic properties.

The Inventors have been able to show, surprisingly and unexpectedly, that it is possible to obtain anhydrous, water-resistant make-up compositions which are highly homogeneous in particular with regard to spreading, by mixing together pigments and at least a large proportion of silicone gum and a silicone oil.

More particularly, a subject of the present invention is an anhydrous, water-resistant cosmetic composition preferably comprising from 2 to 50% of at least one silicone gum, from 10 to 90% of at least one silicone oil, from 0.5 to 15% of at least one pigment and from 0 to 30% of at least one filler.

The compositions according to the invention have the advantage of being stable over time. They are water-resistant since they are anhydrous, and do not contain any water-soluble dyes or solvent. They also have good staying power and do not cause any pulling effect on the skin.

It has furthermore been observed, surprisingly, that the pigments present in the compositions according to the invention were dispersed therein in an unexpectedly very homogeneous manner. This thus has the additional advantage of giving a very uniform and very homogeneous make-up of the skin.

In the following text, the percentages will always be given by weight of active material relative to the total weight of the composition.

In the compositions according to the invention, the silicone gum is preferably present in a proportion ranging from 2% to 50%, more preferably ranging from 4 to 15% and still more preferably ranging from 6% to 9%.

The silicone gum preferably has a molecular weight not greater than 1,500,000. More preferably, the silicone gum has a molecular weight ranging from 200,000 to 1,000,000.

The silicone gum preferably corresponds to the formula:

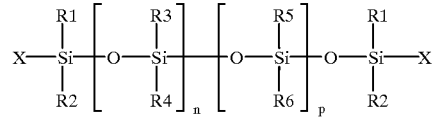

in which:

R1, R2, R5, and R6 each independently represents an alkyl radical having from 1 to 6 carbon atoms;

R3 and R4 each independently represents an alkyl radical having from 1 to 6 carbon atoms or an aryl radical;

X represents an alkyl radical having from 1 to 6 carbon atoms, a hydroxyl radical or a vinyl radical;

n and p are chosen so as to give the silicone gum a viscosity preferably of greater than 100,000 mPa s, and more preferably of greater than 500,000 mPa s.

In general, n and p may have values preferably ranging from 0 to 5000, and more preferably ranging from 0 to 3000.

As silicone gum which may be used according to (the invention, there may preferably be mentioned those for which:

the substituents R1 to R6 and X represent a methyl group, p=0 and n=2700, such as that sold under the name SE30 by the company General Electric;

the substituents R1 to R6 and X represent a methyl group, p=0 and n=2300, such as that sold under the name AK 500000 by the company Wacker;

the substituents R1 to R6 represent a methyl group, the substituent X represents a hydroxyl group, p=0 and n=2700, in solution at a concentration of 13% in cyclopentasiloxane, such as that sold under the name Q2-1401 by the company Dow Corning;

the substituents R1 to R6 represent a methyl group, the substituent X represents a hydroxyl group, p=0 and n=2700, in solution at a concentration of 13% in polydimethylsiloxane, such as that sold under the name Q2-1403 by the company Dow Corning;

the substituents R1, R2, R5, R6 and X represent a methyl group and the substituents R3 and R4 represent an aryl group and p and n are such that the molecular weight of the compound is 600,000, such as that sold under the name 761 by the company Rhone-Poulenc.

The composition according to the invention preferably also comprises at least one silicone oil, in a proportion preferably ranging from 10 to 90%.

A volatile or non-volatile silicone oil may be used.

There may be mentioned, for example:
cyclomethicones D4, D5, D6;
polydimethylsiloxanes (PDMS) of viscosity preferably less than 100 mPa s and more preferably less than 10 mPa s;
alkyldimethicones such as X2-1731 from Dow corning corresponding to the formula:

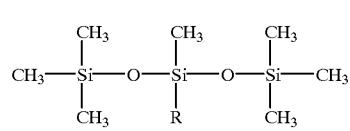

in which R represents the radical $C_nH_{2n+1}$, with n having a value preferably ranging from 3 to 8. The silicone oil is Preferably present in the composition in a proportion ranging from 30 to 70%.

According to a preferred embodiment of the invention, the silicone oil and gum are used in the form of a homogeneous premix consisting of the silicone gum solubilized in the silicone oil.

The composition according to the invention preferably also comprises pigments, in a proportion ranging from 0.5 to 15%, and more preferably ranging from 2 to 8%.

The pigments may be white or coloured and inorganic or organic.

The pigments used in the composition according to the invention may or may not be coated.

U.S. Pat. No. 4,578,566, the disclosure of which is incorporated herein by reference, describes a pretreatment of pigments in order to make them hydrophobic, as a solution in order to introduce large proportions thereof into silicone-based compositions, and in order to ensure better dispersion thereof in the composition. This pretreatment is carried out by coating the pigments with a polysiloxane. Obviously, this pretreatment increases not only the preparation time of the compositions but also their cost.

As has been mentioned above, a particular advantage of the invention lies in the fact that the compositions according to the invention allow a homogeneous and stable dispersion to be obtained, even when pigments which have not been precoated are used.

Among the pigments which may preferably be used, there may be mentioned, without any limiting effect, titanium dioxide ($TiO_2$), zinc oxide (ZnO), zirconium dioxide ($ZrO_2$), black, yellow, red and brown iron oxides, cerium dioxide ($CeO_2$) or alternatively the organic pigments known as barium, strontium, calcium and aluminium lakes.

The composition according to the invention preferably contains 0 to 30% of fillers. These fillers may preferably be inorganic or synthetic and lamellar or non-lamellar.

Talc, mica, silica, kaolin, powders of nylon and of polyethylene, Teflon, starch, titanium mica, natural mother of pearl, boron nitride and hollow microspheres such as Expancel from Nobel Industrie may be mentioned.

The composition according to the invention may also comprise constituents usually used in cosmetic compositions of this type. These constituents are preferably chosen as a function of the desired cosmetic effect for the final composition, such as the covering power, the transparency, the matt quality and/or the satiny appearance.

There may be mentioned, without any limiting effects:
gelling agents, such as the modified clays known under the name bentone, which are sold by the company NL Industrie and used as they are or prepackaged in a gel; hydrophobic silica; waxes, for example polyethylene; aluminum fatty salts. The percentage of gelling agent in the composition will be chosen depending on whether a supple or creamy formula is desired.

vitamins such as tocopherols and derivatives thereof, vitamin A and derivatives thereof, vitamin C and derivatives thereof such as the fatty esters, including the palpitate ester.

sunscreens such as octyl methoxycinnamate (Parsol MCX), 3-benzophenone (Uvinul M40), and butyl-methoxydibenzoylmethane (Parsol 1789).

oily materials such as plant oils, synthetic esters, lecithin, fragrances and essential oils.

The processes for the manufacture of the compositions according to the invention do not differ in any way from the processes conventionally used in cosmetics and with which those skilled in the art are fully familiar.

The compositions according to the invention may be in the form of a product for making up the skin, such as a foundation, a blusher, an eyeshadow or a lipstick, or even in the form of a hair product such as a styling make-up gel.

Examples of compositions according to the invention will now be given by way of example, without any limiting nature being implied.

EXAMPLE 1

Make-up gels having the following compositions (in g) were prepared:

|   |   | Compos. A | Compos. B | Compos. C |
|---|---|---|---|---|
| A) | Polydimethylsiloxane at a concentration of 12–14% in cyclopentasiloxane (Q2-1401 from Dow) | 67.50 | 67.50 | 67.50 |
| B) | $TiO_2$ + iron oxides* | 3.36 | 3.36 | 3.36 |
| C) | cyclopentadimethyl-siloxane | 9.50 | 9.50 | — |
| D) | Gelling agent | | | |
|   | bentone gel IMP (NL Industrie) | 18.64 | 19.14 | — |
|   | bentone gel VS-5 PC (Stearinerie Dubois) | — | 28.14 | 28.14 |
| E) | Fillers | | | |
|   | Expancel microspheres | 1.00 | 1.00 | 1.00 |
|   | Teflon Ceri-dust | — | 2.00 | — |

*Non-coated pigments

A) and B) were mixed together with a spatula and were passed 3 times through a cylinder mill. C), D) and E) were then added with moderate stirring.

Three formulae were obtained, which contained a large proportion of silicone-containing compounds and which made it possible to obtain, after spreading on the skin, a coloured and water-resistant make-up.

Although the pigments used were not precoated, the pigments were fully dispersed in the composition and the make-up obtained was homogeneous.

EXAMPLE 2

Self-tanning compositions having the following compositions (in g) were prepared:

|   |   | Compos. D | Compos. E | Compos. F |
|---|---|---|---|---|
| A) | Polydimethylsiloxane at a concentration of 12–14% in cyclopentasiloxane (Q2-1401) | 67.50 | 67.50 | 67.50 |
| B) | TiO$_2$ + iron oxides* | 3.36 | 3.36 | 3.36 |
| C) | Crosslinked silicone powder in a PDMS (KSG 16 from Shin Etsu) | 20.00 | 10.00 | 10.00 |
|   | bentone gel VS-5 PC (Dubois) | — | 10.00 | — |
|   | Unitwix (United Guardian) | — | — | — |
| D) | Polyvinylidene | 1.00 | 1.00 | 1.00 |
| E) | Silicone oils |   |   |   |
|   | Alkyldimethicone X2-1731 (Dow) | — | — | 5.00 |
|   | Cyclopentadimethylsiloxane | qs 100 | qs 100 | qs 100 |

*Non-coated pigments

Thickened gelled creams were obtained, which were easy and pleasant to apply, and which gave a homogeneous and uniform coloration of natural appearance to the skin.

EXAMPLE 3

Water-resistant silicone-containing self-tanning compositions having the following compositions (in g) were prepared:

|   |   | Compos. G | Compos. H |
|---|---|---|---|
| A) | Silicone oil (AK 500,000 from Wacker) | 10.00 | — |
|   | Polydimethylsiloxane at a concentration of 12–14% in cyclomethicone (Q2-1401 from Dow) | 6.64 | 12.30 |
|   | Polyphenylsiloxane at a concentration of 15% in cyclopentadimethylsiloxane (Silbione 71634 from Rhone-Poulenc) | — | 40.00 |
| B) | TiO$_2$ + iron oxides* | 3.36 | 7.7 |
| C) | Crosslinked silicone powder (KSG 16 from Shin Etsu) | 20.00 | 10.00 |
| D) | Gelling agent (Bentone gel VS38 from Rheox) | — | 18.00 |
| E) | Silicone-containing resin beads (Tospearl 120 from Toshiba) | — | 5.00 |
| F) | Cyclopentadimethylsiloxane | 60.00 | qs 100 |

*Non-coated pigments

Coloured and water-resistant self-tanning compositions were obtained in the form of gels.

EXAMPLE 4

A lipstick having the following composition was prepared:

| Polydimethylsiloxane at a concentration of 12–14% in cyclomethicone (Q2-1401) | 70.00 |
|---|---|
| Crosslinked silicone powder in PDMS (KSG 16 from Shin Etsu) | 10.00 |
| Cyclopentadimethylsiloxane | 10.00 |

-continued

| Silicone-coated titanium oxide | 2.83 |
|---|---|
| Silicone-coated iron oxides | 4.70 |
| D&C red No. 7 | 0.47 |
| Titanium mica | 2.00 |

A fluid gelled cream of red-pink colour with an iridescent effect was obtained, which was smooth upon application and had good staying power.

EXAMPLE 5

A screening tanning fluid having the following composition was prepared:

| Polydimethylsiloxane at a concentration of 12–14% in cyclomethicone (Q2-1401) | 70.00 |
|---|---|
| UV screening agents Parsol MCX from BASF | 7.00 |
| Hydroxy-4-methoxybenzophenone | 2.00 |
| FINSOLV TN (C$_{12}$—C$_{15}$ alkyl benzoate) from Finetex | 9.00 |
| Jojoba oil | 1.00 |
| α-tocopheryl acetate | 1.00 |
| Ethanol | 4.70 |
| Fragrance | 0.30 |
| Crosslinked silicone powder in PDMS (KSG 16 from Shin Etsu) | 10.00 |
| TiO$_2$ + iron oxides (non-coated) | 1.70 |

A shiny, smooth brown-coloured tanning fluid was obtained, which was easy to apply and gave a homogeneous and uniform coloration of natural appearance to the skin.

What is claimed is:

1. A cosmetic composition comprising from 2% to 50% of at least one silicone gum, from 10% to 90% of at least one silicone oil, from 0.5% to 15% of at least one pigment, and from 0 to 30% of at least one filler, wherein said at least one silicone gum is of the formula:

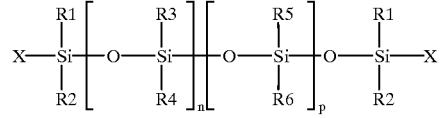

in which

R1, R2, R5 and R6 each independently represents an alkyl radical having from 1 to 6 carbon atoms;

R3 and R4 each independently represents an alkyl radical having from 1 to 6 carbon atoms or an aryl radical;

X represents an alkyl radical having from 1 to 6 carbon atoms, a hydroxyl radical or a vinyl radical; and n and p are selected so as to give said silicone gum a viscosity of greater than 100.000 mPa s, and wherein said composition is anhydrous and water-resistant, and further wherein said composition has cosmetic properties.

2. A composition according to claim 1, wherein said at least one silicone gum is present in an amount which ranges from 4% to 15% by weight relative to the total weight of said composition.

3. A composition according to claim 2, wherein said at least one silicone gum is present in an amount which ranges from 6% to 9%, by weight relative to the total weight of said composition.

4. A composition according to claim 1, wherein n and p have values ranging from 0 to 5000.

5. A composition according to claim 4, wherein n and p have values ranging from 0 to 3000.

6. A composition according to claim 1, wherein said at least one silicone gum is a gum wherein:

the substituents R1 to R6 and X represent a methyl group, p=0 and n=2700;

the substituents R1 to R6 and X represent a methyl group, p=0 and n=2300;

the substituents R1 to R6 represent a methyl group, the substituent X represents a hydroxyl group, p=0 and n =2700; or the substituents R1, R2, R5, R6 and X represent a methyl group, and the substituents R3 and R4 represent an aryl group, and p and n are selected such that the molecular weight of the compound is approximately 600,000.

7. A composition according to claim 1, wherein said at least one silicone oil is present in an amount which ranges from 30% to 70%.

8. A composition according to claim 1, wherein said at least silicone oil is a cyclomethicone, a polydimethylsiloxane of viscosity less than 100 mPa s, or an alkyldimethicone.

9. A composition according to claim 1, wherein said at least one pigment is present in an amount which ranges from 2 to 8% by weight relative to the total weight of the composition.

10. A composition according to claim 1, wherein said at least one pigment is inorganic or organic and is coated or non-coated.

11. A composition according to claim 1, wherein said at least one pigment is titanium dioxide, zinc oxide, zirconium dioxide, black, yellow, red or brown iron oxide, cerium dioxide, an organic pigment or a mixture thereof.

12. A composition according to claim 11, wherein said organic pigment is barium, strontium, calcium or aluminium lakes.

13. A composition according to claim 1, which is in the form of a make-up product or a hair product.

14. A composition according to claim 13, wherein said make-up product is a lipstick, a blusher, an eyeshadow or a foundation and said hair product is a styling make-up gel.

15. A composition according to claim 1, wherein said at least one silicone gum and said at least one silicone oil are present in the form of a homogenous premix consisting of said at least one silicone gum solubilized in said at least one silicone oil.

16. A composition according to claim 1, wherein said at least one filler is inorganic or synthetic and lamellar or non-lamellar.

17. A composition according to claim 1, which further comprises at least one gelling agent, vitamin, sunscreen or oil material.

* * * * *

UNITED STATES PATENT AND TRADEMARK OFFICE
CERTIFICATE OF CORRECTION

PATENT NO.   : 5,985,297
DATED        : November 16, 1999
INVENTORS    : MELLUL et al.

It is certified that error appears in the above-identified patent and that said Letters Patent is hereby corrected as shown below:

Claim 1, col. 6, line 52, "100.000" should read --100,000--.

Signed and Sealed this

Nineteenth Day of September, 2000

Attest:

Q. TODD DICKINSON

Attesting Officer

Director of Patents and Trademarks